(12) United States Patent
Hallinan et al.

(10) Patent No.: US 8,394,987 B2
(45) Date of Patent: *Mar. 12, 2013

(54) METHYL IODIDE REMOVAL FROM ACETIC ACID WASTE STREAM

(75) Inventors: Noel C. Hallinan, Loveland, OH (US); Brian A. Salisbury, Oxford, PA (US); Wayne J. Brtko, Glen Mills, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 336 days.

This patent is subject to a terminal disclaimer.

(21) Appl. No.: 12/802,941

(22) Filed: Jun. 17, 2010

(65) Prior Publication Data

US 2011/0313217 A1  Dec. 22, 2011

(51) Int. Cl.
*C07C 51/12* (2006.01)
*C07C 51/42* (2006.01)

(52) U.S. Cl. ........................................ 562/519; 562/608

(58) Field of Classification Search ............................ None
See application file for complete search history.

(56) References Cited

U.S. PATENT DOCUMENTS

| | | | |
|---|---|---|---|
| 3,769,329 A | 10/1973 | Paulik et al. | |
| 4,102,922 A * | 7/1978 | Price | 562/519 |
| 4,615,806 A * | 10/1986 | Hilton | 210/690 |
| 4,650,615 A * | 3/1987 | Rizkalla | 562/898 |
| 5,139,981 A * | 8/1992 | Kurland | 502/11 |
| 5,220,058 A * | 6/1993 | Fish et al. | 562/608 |
| 5,227,524 A * | 7/1993 | Jones | 562/608 |
| 5,817,869 A | 10/1998 | Hinnenkamp et al. | |
| 5,932,764 A | 8/1999 | Morris et al. | |
| 2009/0229966 A1 | 9/2009 | Hallinan et al. | |

FOREIGN PATENT DOCUMENTS

| EP | 0685 445 | 12/1995 |
|---|---|---|
| EP | 685445 | * 12/1995 |

* cited by examiner

*Primary Examiner* — Karl J Puttlitz

(57) ABSTRACT

The invention is a method of removing methyl iodide from an alkane distillation bottoms stream of an acetic acid production process. The method comprises contacting the alkane distillation bottoms stream in the liquid phase with a phosphine or a phosphine-functionalized support, and recovering a treated alkane distillation bottoms stream having a reduced methyl iodide content.

12 Claims, No Drawings

METHYL IODIDE REMOVAL FROM ACETIC ACID WASTE STREAM

FIELD OF THE INVENTION

This invention relates to the removal of methyl iodide from an acetic acid waste stream.

BACKGROUND OF THE INVENTION

Acetic acid is a well-known chemical that is available from Lyondell Chemical Company and other producers. Acetic acid is commercially produced by methanol carbonylation in the presence of a rhodium catalyst, methyl iodide, methyl acetate, and water (the "Monsanto process"), see U.S. Pat. No. 3,769,329. Catalyst stabilizers such as lithium iodide or pentavalent Group VA oxides may also be added to the carbonylation reaction. The process results in a high selectivity to acetic acid.

The methanol carbonylation process results in the formation of hydrocarbon impurities such as alkanes and aromatics. The alkanes are typically removed from the process in an alkane distillation column that separates a vapor stream comprising a majority of methyl iodide from a bottoms stream comprising acetic acid, methyl acetate, methyl iodide, and the hydrocarbon impurities. The bottoms stream is typically disposed as waste. Since methyl iodide is an expensive material, previous methods have been disclosed for recovering methyl iodide from the bottoms waste stream. For instance, U.S. Pat. Appl. Pub. No. 2009/0229966 teaches an acetic acid production process that comprises extracting the alkane distillation bottoms stream with water, an acetic acid aqueous solution, or with a methanol aqueous solution, and forming an organic phase comprising the majority of the hydrocarbon impurity and an aqueous phase comprising the majority of water, acetic acid, methyl iodide, and optional methanol. The aqueous phase is recycled to the methanol carbonylation reaction.

Methods for removing alkanes from acetic acid while trying to minimize methyl iodide loss are also known. For instance, U.S. Pat. No. 4,102,922 discloses an alkane removal method in which a slip stream from the heavy phase which comprises methyl iodide, acetic acid, water and alkanes is fed to the alkane distillation column with an overhead temperature of about 75° C. and a bottoms temperature of about 142° C. The bottoms temperature is run significantly higher than the overhead in order to minimize methyl iodide loss to the bottoms stream. The overhead of the alkane distillation, comprising mainly methyl iodide, is recycled to the reaction section. The bottoms stream comprising about 50% acetic acid and about 40% alkanes is removed from the system as waste.

A widely disclosed method teaches removal of iodide impurities from acetic acid by adsorption. A variety of solid adsorbents have been described, and typically contain reactive metals, such as silver, mercury, copper, lead, thallium, palladium, to remove iodide from solution. U.S. Pat. Nos. 4,615,806 and 5,139,981, and 5,227,524 disclose the use of macroreticulated, strong acid cationic exchange resins that contain silver or mercury. The iodide reacts with the resin bound metal and is removed from the acetic acid stream. U.S. Pat. No. 5,220,058 discloses the use of ion exchange resins having metal exchanged thiol functional groups to remove iodide impurities from acetic acid and/or acetic anhydride. The thiol functionality of the ion exchange resin is taught to have been exchanged with silver, palladium, or mercury. European Patent No. 685,445 teaches contacting an iodide containing acetic acid stream with a polyvinylpyridine at elevated temperatures to remove the iodides. U.S. Pat. No. 3,943,229 discloses removing iodide compounds from gaseous streams by contact with certain cross-linked acrylic anion exchange resins. In addition, U.S. Pat. No. 4,650,615 teaches the purification of carboxylic acid anhydrides, such as acetic anhydride, contaminated with halogen and halide values by treating the anhydrides with a phenyl or an alkyl phosphine in the absence of copper, zinc, silver, and cadmium or their compounds and distilling to recover purified anhydrides.

In sum, new methods for the removal of methyl iodide from the alkane distillation bottoms waste stream are needed. We have discovered an effective, convenient method to remove methyl iodide.

SUMMARY OF THE INVENTION

The invention is a method of removing methyl iodide from an alkane distillation bottoms stream of an acetic acid production process. The method comprises contacting the alkane distillation bottoms stream in the liquid phase with a phosphine or a phosphine-functionalized support, and recovering a treated alkane distillation bottoms stream having a reduced methyl iodide content.

DETAILED DESCRIPTION OF THE INVENTION

Acetic acid is a well-known chemical that is available from Lyondell Chemical Company and other producers. Acetic acid is typically produced by a methanol carbonylation process. The methanol carbonylation reaction to produce acetic acid is described in U.S. Pat. No. 3,769,329.

Methanol and carbon monoxide are fed to a carbonylation reactor. The methanol feed to the carbonylation reaction can come from a syngas-methanol facility or any other source. Suitable catalysts include rhodium and iridium catalysts. Rhodium catalysts are preferred. Suitable rhodium catalysts are taught, for example, by U.S. Pat. No. 5,817,869. Typical rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, and mixtures thereof.

Suitable iridium catalysts are taught, for example, by U.S. Pat. No. 5,932,764. Typical iridium catalysts include iridium metal and iridium compounds. Examples of iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The carbonylation reaction is performed in the presence of methyl iodide. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Preferably, the carbonylation reaction is performed in the presence of a catalyst stabilizer. Suitable catalyst stabilizers include metal iodide salts such as lithium iodide or non-salt stabilizers such as pentavalent Group VA oxides. See, for example, U.S. Pat. No. 5,817,869. Phosphine oxides are more preferred. Triphenylphosphine oxides are most preferred.

The carbonylation reaction is preferably performed in the presence of water. Preferably, the concentration of water is from about 2 wt % to about 14 wt % based on the total weight of the reaction medium, more preferably from about 2 wt % to about 10 wt %, and most preferably from about 4 wt % to about 8 wt %.

The carbonylation reaction is preferably performed in the presence of methyl acetate. Methyl acetate can be formed in situ or can be added as a starting material to the reaction mixture. Preferably, the concentration of methyl acetate is from about 2 wt % to about 20 wt % based on the total weight of the reaction medium, more preferably from about 2 wt % to about 16 wt %, and most preferably from about 2 wt % to about 8 wt %. Hydrogen may also be fed into the carbonylation reactor. Addition of hydrogen can enhance the carbonylation efficiency. Preferably, the concentration of hydrogen is from about 0.1 mol. % to about 5 mol. % of carbon monoxide in the reactor, and more preferably from about 0.3 mol. % to about 3 mol. %.

The carbonylation reaction is preferably performed at a temperature within the range of about 150° C. to about 250° C., and more preferably within the range of about 150° C. to about 200° C. The carbonylation reaction is preferably performed under a pressure within the range of about 200 psig to about 2,000 psig, and more preferably within the range of about 300 psig to about 500 psig.

The methanol carbonylation reaction produces a crude acetic acid reaction effluent. The crude acetic acid reaction effluent is subjected to one or more purification steps in order to remove impurities such as hydrocarbons and produce an acetic acid product stream.

Hydrocarbon impurities are produced by the side reactions of methanol carbonylation. Examples of hydrocarbon impurities include alkanes, alkenes, and aromatics. Alkane impurities commonly produced in methanol carbonylation are $C_3$-$C_{12}$ alkanes including propane, butane, pentane, 2-methylbutane, 2,3-dimethylbutane, 2-methyl pentane, 3-methylpentane, hexane, octane, decane, cyclohexane, the like, and mixtures thereof. Commonly seen alkenes include propylene, butene, octene, the like, and mixtures thereof. Commonly seen aromatics include benzene, n-propylbenzene, toluene, xylene, the like, and mixtures thereof.

Thus, preferably the method of the invention comprises first reacting methanol and carbon monoxide in the presence of a catalyst and methyl iodide to produce a crude acetic acid effluent; distilling the crude acetic acid effluent in one or more distillation columns to produce an acetic acid stream and a methyl iodide stream comprising methyl iodide, water, acetic acid, methyl acetate, and hydrocarbon impurities; decanting the methyl iodide stream to produce an aqueous stream comprising water, acetic acid and methyl acetate and a heavy organic stream comprising methyl iodide, hydrocarbons, acetic acid, and methyl acetate; distilling the heavy organic stream in an alkane distillation column to produce an overhead stream comprising methyl iodide and an alkane distillation bottoms stream comprising hydrocarbon impurities, acetic acid, methyl acetate, and methyl iodide; and contacting the alkane distillation bottoms stream in the liquid phase with a phosphine or a phosphine-functionalized support, and recovering a treated alkane distillation bottoms stream having a reduced methyl iodide content.

Following the carbonylation of methanol, the crude acetic acid product mixture is preferably first flash distilled. The flash distillation step separates acetic acid, methanol, and methyl iodide as a vapor fraction from a liquid fraction comprising the catalyst and the catalyst stabilizer, if utilized. The liquid fraction is preferably recycled back the methanol carbonylation reaction.

The vapor fraction is then preferably passed to a distillation column.

The distillation column, the so-called "light ends distillation," separates an overhead methyl iodide stream comprising methyl iodide, water, acetic acid, methyl acetate, and hydrocarbon impurities from an acetic acid stream comprising acetic acid, a small amount of water, and some heavy impurities such as propionic acid. The acetic acid stream may be passed to a drying column to remove water and then be subjected to distillation, the so-called "heavy ends distillation," to remove the heavy impurities.

The overhead methyl iodide stream from the light ends distillation usually comprises from about 60 wt % to about 90 wt % of methyl iodide, from about 5 wt % to about 15 wt % of methyl acetate, from about 1 wt % to about 10 wt % of acetic acid, 1 wt % or less of water, and from about 1 wt % to about 10 wt % of hydrocarbon impurities based on the total weight of the overhead.

The overhead methyl iodide stream is preferably condensed and separated in a decanter to a light, aqueous phase and a heavy, organic phase. The heavy, organic phase comprises predominantly methyl iodide (greater than 50%) and the hydrocarbon impurities, with minor amounts of acetic acid and methyl acetate. The is light, aqueous phase comprises predominantly water (greater than 50%), acetic acid, and methyl acetate. The aqueous phase is usually recycled to the reactor or to the light ends distillation.

At least a portion of the heavy, organic phase is preferably distilled to form a vapor stream comprising the majority of methyl iodide (over 50% of the methyl iodide from the heavy organic phase) and a bottoms stream comprising the majority of acetic acid, methyl acetate, methyl iodide, and the hydrocarbon impurities (typically over 50% of each component from the heavy organic phase). This distillation is the so-called "alkane distillation" in the industry. The bottoms temperature of the alkane distillation is preferably above about 100° C., more preferably from 110° C. to 200° C., and most preferably from 120° C. to 160° C. The overhead temperature of the alkane distillation is preferably below about 75° C. so that there is no significant amount of hydrocarbon impurities coming out with the vapor stream, more preferably within the range of about 43° C. (boiling point of methyl iodide) to about 75° C., and most preferably within the range of about 43° C. to about 60° C. The particularly preferred overhead temperature of the alkane distillation is within the range of about 43° C. to about 45° C. The closer the overhead temperature of the alkane distillation to the boiling point of methyl iodide, the less the amount of hydrocarbon impurities existing in the vapor stream. The vapor stream is recycled to the carbonylation reaction. Lowering the overhead temperature of the alkane distillation, although reducing the hydrocarbon impurities in the vapor stream, results in a higher concentration of methyl iodide in the alkane distillation bottoms stream.

According to current industrial practice, the alkane distillation bottoms stream is disposed as a waste. Thus, an increased amount of methyl iodide, an expensive material, is wasted. The method of the invention comprises the removal of methyl iodide from the alkane distillation bottoms stream.

According to the method of the invention, the alkane distillation bottoms stream is contacted in the liquid phase with a phosphine or a phosphine-functionalized support, and then a treated alkane distillation bottoms stream having a reduced methyl iodide content is recovered. Preferably, the contacting step removes at least 25 percent of the methyl iodide content from the alkane distillation bottoms stream, and more preferably at least 50 percent. Preferably, the contacting step removes at least 0.4 mole equivalents methyl iodide (moles MeI removed/moles active phosphine), and more preferably at least 0.7 mole equivalents.

In accordance with the present invention, the alkane distillation bottoms stream is contacted in the liquid phase with a phosphine or a phosphine-functionalized support adsorbent whereby methyl iodide is retained on the phosphine-functionalized support or a methyl phosphonium iodide compound is produced. The methyl iodide reduced bottoms stream may then be conveniently separated and disposed as waste.

The phosphine useful in the invention is preferably a trisubstituted tertiary phosphine that is represented by the formula:

$(R^1)_3P$ wherein $R^1$ is an aryl or alkyl group. Preferably, the phosphine is a dialkylarylphosphine, an alkyldiarylphosphine, a triarylphosphine, or mixtures thereof. Suitable aliphatic $R^1$ groups include methyl, ethyl, n-butyl, sec-butyl, octyl, and decyl. Suitable aromatic $R^1$ groups include phenyl, tolyl, and naphthyl. The $R^1$ groups may be the same or are different, but preferably are the same. Preferably, the tertiary phosphine is a trisubstituted aryl phosphine. More preferably, the tertiary phosphine is triphenylphosphine or tritolylphosphine. Triphenylphosphine is particularly preferred.

The phosphine-functionalized support useful in the invention is a solid material that consists of a support which has been functionalized with a phosphine group. Supports are well-known in the art. There are no particular restrictions on the types of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, ceria, niobium oxides, tantalum oxides, molybdenum oxides, tungsten oxides, amorphous titania-silica, amorphous zirconia-silica, amorphous niobia-silica, ceria-silica, and the like. Preferred organic polymer resins include polystyrene, styrene-divinylbenzene copolymers, crosslinked polyethyleneimines, and polybenzimidazole. Suitable supports also include organic polymer resins grafted onto inorganic oxide supports, such as polyethylenimine-silica. Preferably, the support is an inorganic oxide. Particularly preferred inorganic oxide supports include silica, alumina, titania, zirconia, niobium oxides, tantalum oxides, titania-silica, zirconia-silica, alumina-silica, niobia-silica, and the like. Silica, alumina, titania, zirconia, titania-silica, zirconia-silica, and alumina-silica are most preferred.

The phosphine unit of the phosphine-functionalized support is preferably a tertiary phosphine. Preferred tertiary phosphines include trialkylphosphines, dialkylarylphosphines, alkyldiarylphosphines, and triarylphosphines. Alkyldiarylphosphines and triarylphosphines are particularly preferred. Most preferred include methyldiphenylphosphine, ethyldiphenylphosphine, n-propyldiphenylphosphine, n-butyldiphenylphosphine, and triphenylphosphine. Specific commercially available phosphine-functionalized supports include diphenylphosphinoethyl-functionalized silica gel and diphenylphosphine polystyrene resin (both available from Sigma-Aldrich).

In general, suitable phosphine-functionalized supports are further characterized by having a relatively large surface area in relation to their mass. The phosphine-functionalized supports for purpose of this invention preferably have a surface area of at least 100 m$^2$/g, and more preferably the average surface area is from 400 m$^2$/g to 1500 m$^2$/g.

Phosphine-functionalized supports may be prepared by any suitable method. For instance, a lithiated phosphine such as diphenylphosphine lithium (Ph$_2$PLi) may be reacted with resin-bound phenyl halide to give a phosphine-functionalized support (triphenylphosphine resin). Phosphine-functionalized supports may also be formed by the copolymerization of styrene, divinylbenzene, and a phosphine-substituted styrene such as diphenylphosphinostyrene. An inorganic oxide-functionalized support can be prepared by reacting an inorganic oxide such as silica with a phosphinoalkylsilane compound such as diphenylphosphinoethyltriethoxysilane to produce a diphenylphosphinoethyl-functionalized silica.

The alkane distillation bottoms stream is contacted in the liquid phase with a phosphine or a phosphine-functionalized support. If contacted with a phosphine-functionalized support, the adsorptive contact is preferably carried out by passing the alkane distillation bottoms stream through a bed of phosphine-functionalized support. The invention may be carried out in a continuous or batch-wise fashion in accordance with known procedures. Continuous operation is preferred, as is the use of a plurality of adsorbent contact zones. When a plurality of adsorbent contact zones are used, one zone may be in use while adsorbent in a second zone is regenerated. The use of three contact zones is particularly preferred, with two zones in use at the same time, one a lead contact zone and the second a polishing zone, while the third zone is regenerated.

The adsorptive contact is conveniently carried out at moderate temperatures. Suitable temperatures are in the range of about 10° C. to 100° C., preferably 15° C. to 80° C. Flow rates of about 0.005 to 50 volumes of acetic acid per volume of adsorbent per hour are preferred, more preferably about 0.02-5. In general, slower feed flow rate reduces product impurity at a given bed-volume. Therefore, flow rate may be optimized depending on the volume of adsorbent utilized in the method.

The phosphine-functionalized support retains the methyl iodide adsorbed thereon and purified alkane distillation bottoms stream can be separated. Initially, there can be substantially complete removal of methyl iodide but over the course of time the phosphine-functionalized support gradually becomes less effective for the removal of methyl iodide.

Thus, when the separation efficiency of the phosphine-functionalized support has fallen below a desired point, the adsorbent is preferably regenerated. The adsorbent is preferably regenerated by a high temperature thermal heating, followed by refunctionalization of the support with the phosphine. For instance, used 2-diphenylphosphinoethyl-functionalized silica may be oxidized and/or reduced at temperatures ranging from 250° C. to 500° C., and then refunctionalized with diphenylphosphinoethyltriethoxysilane to produce regenerated 2-diphenylphosphinoethyl-functionalized silica. It is advantageous to employ a plurality of parallel contact zones such that while one zone is being regenerated the feed is passed through a zone containing fresh or regenerated contact material so that optimum impurities removal can be achieved. Preferably, during the high temperature thermal heating of the adsorbent, the methyl iodide that is liberated is captured and recycled back to the reaction section.

If the alkane distillation bottoms stream is contacted with a phosphine, the phosphine is preferably added to the alkane distillation bottoms stream at moderate temperatures. Suitable temperatures are in the range of about 10° C. to 100° C., preferably 15° C. to 80° C. The phosphine reacts with the methyl iodide in solution to produce a methyl phosphonium iodide species; for example, the reaction of triphenylphosphine and methyl iodide produces methyl triphenylphosphonium iodide. This compound is a valuable starting material used in the pharmaceutical and small molecule industries to make olefins from carbonyls using the Wittig reaction. The methyl phosphonium iodide may be recovered from the alkane distillation bottoms stream by any suitable process, but is preferably recovered by filtration as the methyl phosphonium iodide species is insoluble in the alkane distillation bottoms stream.

Following the methyl iodide removal method by contact with a phosphine or a phosphine-functionalized support, a treated alkane distillation bottoms stream having decreased methyl iodide compound impurities content is recovered. Preferably, the methyl iodide reduced bottoms stream may then be conveniently disposed as waste.

The following examples merely illustrate the invention. Those skilled in the art will recognize many variations that are within the spirit of the invention and scope of the claims.

EXAMPLES

Adsorption Runs

Example 1

A solution (2.54 g) composed of 60.79 wt % dodecane, 6.32 wt % acetic acid, 13.96 wt % methyl acetate and 18.93 wt % methyl iodide is added to a 10 mL vial at 20° C. Polystyrene-bound triphenylphosphine (0.38 g of 3.0 mmol/g) is added to the vial. After an initial brief shaking, the vial is set aside and sampled by syringe several times over a period of 120 minutes. Sample analysis is carried out using an Analect Diamond 20 FTIR equipped with a 0.074-mm path length transmission cell which contained zinc selenide windows. Methyl iodide concentration in the 120 minute sample is 14.23 wt % and corresponds to removal of 0.73 mole equivalents.

Example 2

A solution (6.24 g) composed of 91.23 wt % decane and 8.77 wt % methyl iodide is added to a 10 mL vial at 20° C. Triphenylphosphine (1.12 g) is added to the vial. After an initial brief shaking, the vial is set aside and sampled by syringe several times over a period of 105 minutes. Methyl iodide concentration in the 105 minute sample, using the analysis of Example 1, is 4.39 wt % and corresponds to removal of 0.45 mole equivalents.

Example 3

A solution (1.64 g) composed of 67.16 wt % dodecane, 5.97 wt % acetic acid, 12.43 wt % methyl acetate and 14.44 wt % methyl iodide is added to a 10 mL vial. 2-Diphenylphosphinoethyl functionalized silica gel (0.74 g of 1.05 mmol/g) is added to the vial. After an initial brief shaking, the vial was set aside and sampled by syringe twice over a period of 40 minutes. Methyl iodide concentration in the 40 minute sample, using the analysis of Example 1, is 8.05 wt % and corresponds to removal of 0.93 mole equivalents.

We claim:

1. A method of removing methyl iodide from an alkane distillation bottoms stream of an acetic acid production process, which comprises contacting the alkane distillation bottoms stream in the liquid phase with a phosphine-functionalized support, and recovering a treated alkane distillation bottoms stream having a reduced methyl iodide content.

2. The method of claim 1 wherein the phosphine-functionalized support is a tertiary phosphine-functionalized support.

3. The method of claim 2 wherein the tertiary phosphine is an alkyldiarylphosphine.

4. The method of claim 1 wherein the Support is an inorganic oxide.

5. The method of claim 4 wherein the inorganic oxide is selected from the group consisting of silica, alumina, titania, zirconia, titania-silica, zirconia-silica, alumina-silica, and mixtures thereof.

6. A method which comprises:
   (1) reacting methanol and carbon monoxide in the presence of a catalyst and methyl iodide to produce a crude acetic acid effluent;
   (2) distilling the crude acetic acid effluent in one or more distillation columns to produce an acetic acid stream and a methyl iodide stream comprising methyl iodide, water, acetic acid, methyl acetate, and hydrocarbon impurities:
   (3) decanting the methyl iodide stream to produce an aqueous stream comprising water, acetic acid and methyl acetate and a heavy organic stream comprising methyl iodide, hydrocarbon impurities, acetic acid, and methyl acetate;
   (4) distilling the heavy organic stream in an alkane distillation column to produce an overhead stream comprising methyl iodide and an alkane distillation bottoms stream comprising hydrocarbon impurities, acetic acid, methyl acetate, and methyl iodide; and
   (5) contacting the alkane distillation bottoms stream in the liquid phase with a phosphine-functionalized support, and recovering a treated alkane distillation bottoms stream having a reduced methyl iodide content, 7. The method of claim 6 wherein the phosphine-functionalized support is a tertiary phosphine-functionalized support.

8. The method of claim 7 wherein the tertiary phosphine is an alkyldiarylphosphine, 9. The method of claim 6 wherein the support is an inorganic oxide.

10. The method of claim 9 wherein the inorganic oxide is selected from the group consisting of silica, alumina, titania, zirconia, titania-silica, zirconia-silica, alumina-silica, and mixtures thereof 11. The method of claim 1, wherein the phosphine-functionalized support comprises a surface area of from 400 to 1500.

12. The method of claim 6, wherein the phosphine-functionalized support comprises a surface area of from 400 to 1500.

* * * * *